US008647115B2

(12) United States Patent
Boehm et al.

(10) Patent No.: US 8,647,115 B2
(45) Date of Patent: Feb. 11, 2014

(54) SYRINGES FOR DISPENSING MULTI-COMPONENT MATERIAL

(75) Inventors: Andreas J. Boehm, Reichling (DE); Marc Peuker, Schondorf (DE); Alexander Walter, Pürgen (DE); Brigitte Rohmer, Landsberg am Lech (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/147,606

(22) PCT Filed: Feb. 8, 2010

(86) PCT No.: PCT/US2010/023450
§ 371 (c)(1),
(2), (4) Date: Aug. 3, 2011

(87) PCT Pub. No.: WO2010/093575
PCT Pub. Date: Aug. 19, 2010

(65) Prior Publication Data
US 2011/0294091 A1    Dec. 1, 2011

(30) Foreign Application Priority Data
Feb. 13, 2009    (GB) ................................... 0902354.0

(51) Int. Cl.
*A61C 5/04*    (2006.01)
(52) U.S. Cl.
USPC .......................................................... 433/90
(58) Field of Classification Search
USPC ............... 433/81, 90, 80; 222/325–327, 386; 604/82–92, 191; 285/322, 243, 257; 137/15.2, 15.18, 15.22–15.24, 625.46, 137/625.48, 874–876, 887
See application file for complete search history.

(56) References Cited

U.S. PATENT DOCUMENTS

| 4,930,920 A | 6/1990 | Fitzig |
| 4,995,540 A * | 2/1991 | Colin et al. ................... 222/132 |

(Continued)

FOREIGN PATENT DOCUMENTS

| CA | 2298984 | 3/1999 |
| CA | 2441479 | 9/2002 |

(Continued)

OTHER PUBLICATIONS

International Search Report PCT/US2010/023450 Feb. 10, 2011, 6 pgs.

(Continued)

*Primary Examiner* — Cris L Rodriguez
*Assistant Examiner* — Mirayda A Aponte
(74) *Attorney, Agent, or Firm* — Nicole J. Einerson

(57) ABSTRACT

A syringe for dispensing a multi-component material. The syringe can include a cartridge having a first end and a second end, and respective compartments for components of the multi-component material; a static mixer connected to the first end of the cartridge, the mixer having a dispensing outlet; and a plunger assembly that is movable into the syringe cartridge at the second end to dispense material from the first end. A connection between the static mixer and the first end of the syringe cartridge includes a flow-directing mechanism having a venting position in which the cartridge compartments are cut off from the static mixer and are in communication independently with respective venting outlets, and a dispensing position in which the cartridge compartments are in communication with the static mixer and are cut off from the venting outlets.

21 Claims, 8 Drawing Sheets

(56) References Cited

U.S. PATENT DOCUMENTS

| | | | |
|---|---|---|---|
| D322,317 S | 12/1991 | Fischer | |
| 5,161,715 A | 11/1992 | Giannuzzi | |
| 5,190,526 A | 3/1993 | Murray | |
| 5,242,414 A | 9/1993 | Fischell | |
| 5,257,632 A | 11/1993 | Turkel | |
| 5,324,265 A | 6/1994 | Murray | |
| 5,328,462 A | 7/1994 | Fischer | |
| D353,199 S | 12/1994 | Frohnmayer | |
| 5,378,233 A | 1/1995 | Haber | |
| 5,387,103 A | 2/1995 | Fischer | |
| D357,065 S | 4/1995 | Castellini | |
| 5,643,206 A * | 7/1997 | Fischer | 604/82 |
| 5,665,066 A * | 9/1997 | Fischer | 604/82 |
| 5,697,918 A * | 12/1997 | Fischer et al. | 604/227 |
| D409,305 S | 5/1999 | Martin | |
| 6,047,861 A * | 4/2000 | Vidal et al. | 222/137 |
| 6,048,201 A * | 4/2000 | Zwingenberger | 433/90 |
| 6,116,900 A | 9/2000 | Ostler | |
| 6,197,006 B1 | 3/2001 | Wiklund | |
| 6,283,946 B1 | 9/2001 | Fischer | |
| 6,398,761 B1 | 6/2002 | Bills | |
| 6,415,679 B1 | 7/2002 | Chiodo | |
| 6,484,904 B1 | 11/2002 | Horner | |
| 6,732,887 B2 | 5/2004 | Bills | |
| 6,874,661 B2 | 4/2005 | Timmerman | |
| D520,807 S | 5/2006 | Morgan | |
| D556,320 S | 11/2007 | Boclet | |
| 7,367,475 B2 | 5/2008 | Hörth | |
| 7,424,318 B2 | 9/2008 | Brister | |
| 7,467,003 B2 | 12/2008 | Brister | |
| 7,530,808 B2 | 5/2009 | Cao | |
| 7,604,626 B2 * | 10/2009 | McIntosh et al. | 604/506 |
| 7,740,479 B2 | 6/2010 | Allred | |
| 7,761,130 B2 | 7/2010 | Simpson | |
| 7,766,191 B2 | 8/2010 | Jackson | |
| 7,831,287 B2 | 11/2010 | Brister | |
| 7,882,983 B2 * | 2/2011 | Reidt et al. | 222/137 |
| 7,883,501 B2 * | 2/2011 | McIntosh et al. | 604/506 |
| 7,954,672 B2 * | 6/2011 | Keller | 222/137 |
| D645,140 S | 9/2011 | Peuker | |
| D645,959 S | 9/2011 | Peuker | |
| D650,897 S | 12/2011 | Peuker | |
| D650,898 S | 12/2011 | Peuker | |
| D650,899 S | 12/2011 | Peuker | |
| D650,900 S | 12/2011 | Peuker | |
| 8,074,843 B2 | 12/2011 | Keller | |
| 2001/0039401 A1 | 11/2001 | Ferguson | |
| 2002/0001790 A1 | 1/2002 | Qualliotine | |
| 2002/0099355 A1 | 7/2002 | Chen | |
| 2002/0146662 A1 * | 10/2002 | Radl et al. | 433/90 |
| 2002/0183698 A1 | 12/2002 | Quinn | |
| 2003/0004465 A1 | 1/2003 | Ferguson | |
| 2003/0060777 A1 | 3/2003 | Benz | |
| 2004/0024361 A1 | 2/2004 | Fago | |
| 2004/0064102 A1 * | 4/2004 | Yamada | 604/191 |
| 2004/0116875 A1 | 6/2004 | Fischer | |
| 2004/0234923 A1 | 11/2004 | Larsen | |
| 2004/0236281 A1 | 11/2004 | Popvsky | |
| 2005/0197630 A1 | 9/2005 | Wicklund | |
| 2005/0202365 A1 | 9/2005 | Cao | |
| 2005/0228347 A1 * | 10/2005 | Verkaart | 604/191 |
| 2006/0009742 A1 | 1/2006 | Solazzo | |
| 2006/0178618 A1 | 8/2006 | Lowenstein | |
| 2006/0253082 A1 * | 11/2006 | McIntosh et al. | 604/191 |
| 2006/0287639 A1 | 12/2006 | Sharp | |
| 2007/0048688 A1 * | 3/2007 | Pauser et al. | 433/90 |
| 2007/0051750 A1 | 3/2007 | Suchan | |
| 2007/0060878 A1 | 3/2007 | Bonnette | |
| 2007/0166660 A1 * | 7/2007 | Peuker et al. | 433/89 |
| 2007/0167868 A1 | 7/2007 | Sauer | |
| 2007/0250005 A1 | 10/2007 | Fago | |
| 2007/0260258 A1 | 11/2007 | Sommerich | |
| 2007/0270743 A1 | 11/2007 | Ackerman | |
| 2008/0083782 A1 | 4/2008 | Heusser | |
| 2009/0264831 A1 * | 10/2009 | Thompson et al. | 604/191 |
| 2010/0028831 A1 | 2/2010 | Pierson | |
| 2010/0261139 A1 * | 10/2010 | Leiner et al. | 433/90 |
| 2011/0021982 A1 * | 1/2011 | Keller | 604/82 |
| 2011/0295212 A1 * | 12/2011 | Greter et al. | 604/191 |
| 2011/0301545 A1 * | 12/2011 | Nalesso et al. | 604/191 |

FOREIGN PATENT DOCUMENTS

| | | |
|---|---|---|
| CA | 2587777 | 5/2006 |
| CN | 1463760 | 12/2003 |
| CZ | 1998-2233 | 2/2000 |
| DE | 1938028 | 1/1971 |
| DE | 3729979 | 3/1989 |
| DE | 3730910 | 3/1989 |
| DE | 3731703 | 4/1989 |
| EP | 0372892 | 6/1990 |
| EP | 1134001 | 9/2001 |
| EP | 1170055 | 1/2002 |
| EP | 1440706 | 7/2004 |
| FR | 2701211 | 8/1994 |
| FR | 2769491 | 4/1999 |
| FR | 2770407 | 5/1999 |
| FR | 2784033 | 4/2000 |
| FR | 2784034 | 4/2000 |
| GB | 2339545 | 12/2002 |
| IL | 156556 | 2/2010 |
| TW | 527933 | 4/2003 |
| WO | WO 94/08638 | 4/1994 |
| WO | WO 96/08440 | 3/1996 |
| WO | WO 98/13094 | 4/1998 |
| WO | WO 00/07539 | 2/2000 |
| WO | WO 00/69488 | 11/2000 |
| WO | WO 2004/058326 | 7/2004 |
| WO | WO 2004/069037 | 8/2004 |
| WO | WO 2005/016170 | 2/2005 |
| WO | WO 2005/016783 | 2/2005 |
| WO | WO 2005016783 A1 * | 2/2005 |
| WO | WO 2007/056051 | 5/2007 |
| WO | WO 2007/095769 | 8/2007 |
| WO | WO 2007/104037 | 9/2007 |
| WO | WO 2008/048568 | 4/2008 |
| WO | WO 2008/051925 | 5/2008 |
| WO | WO 2010/093575 | 8/2010 |

OTHER PUBLICATIONS

Search Report in Application No. GB0902354.0, May 22, 2009, 4 pgs.
Design U.S. Appl. No. 29/366,901, filed Jul. 30, 2010.
Design U.S. Appl. No. 29/366,904, filed Jul. 30, 2010.
Design U.S. Appl. No. 29/366,906, filed Jul. 30, 2010.
Design U.S. Appl. No. 29/366,907, filed Jul. 30, 2010.

* cited by examiner

SYRINGES FOR DISPENSING MULTI-COMPONENT MATERIAL

CROSS REFERENCE TO RELATED APPLICATIONS

This is a national stage filing under 35 U.S.C. 371 of PCT/US2010/023450, filed Feb. 8, 2010, which claims priority to GB Application No. 0902354.0, filed Feb. 13, 2009, the disclosure of which is incorporated by reference in their entirety herein.

The present invention relates to syringes for dispensing multi-component materials, in particular syringes comprising a cartridge having respective compartments for components of a multi-component material. The invention is concerned, more especially, with unit-dose syringes of that type, including unit-dose syringes for dispensing dental materials.

Syringes that comprise a cartridge having respective compartments for components of a multi-component material are well known. In one form, a static mixer is connected at the output end of the syringe cartridge to receive the material components dispensed from the cartridge, typically by a plunger assembly that is moved into the cartridge at the opposite end. The components are mixed together during their passage through the static mixer, and the resulting multi-component material is dispensed through a nozzle, also known as a mixing tip, at the output end of the mixer.

In the field of dentistry, it is known to use an applicator to dispense dental impression material from a two-compartment supply cartridge provided, as in the syringe described above, with a static mixer and a mixing tip. The compartments of the supply cartridge contain components of the impression material (typically, a base paste and a catalyst respectively), which are dispensed from the supply cartridge in the required relative amounts by a plunger assembly in the applicator. An applicator of that type is available, together with replacement cartridges, static mixers and mixing tips, from 3M ESPE AG of Seefeld, Germany under the trade name "Garant".

Small-size syringes, especially unit-dose syringes, are increasingly being proposed for use in the field of dentistry to dispense materials that are formed from two or more components which are to be mixed together only immediately prior to use. Such small-size syringes are particularly suitable for intra-oral applications when only small amounts of material are required, for example when applying wash material for a dental impression. One small-size syringe is available, for example, under the trade name "BFC" from Ho Dental Company of Las Vegas, Nev., USA, and others are described in WO 2007/095769 (MIXPAC SYSTEMS AG) and WO 2005/016170 (3M ESPE AG).

Small-size syringes offer the advantage of being easy to manipulate, more suited to the size of a patient's mouth, and disposable after use. In addition, if they are loaded with material only as required for a particular dental procedure, problems associated with longer term storage of dental materials (which may occur when a re-usable syringe is used) can be avoided. Those problems include, for example, inadvertent mixing and hardening of the materials making the syringe unusable, and the risk of materials deteriorating while they are being stored.

The present invention is concerned with improving syringes for dispensing multi-component materials, especially dental syringes and more especially unit-dose syringes. In particular, the present invention is concerned with facilitating the filling of a syringe with components of the multi-component material to be dispensed, and the subsequent temporary storage of the components within the syringe if required.

The present invention provides a syringe for dispensing a multi-component material, the syringe comprising:
a syringe cartridge having a first end and a second end, and respective compartments for components of the multi-component material;
a static mixer connected to the first end of the cartridge, the mixer having a dispensing outlet; and
a plunger assembly that is movable into the syringe cartridge at the second end to dispense material from the first end. The connection between the static mixer and the first end of the syringe cartridge comprises a flow-directing mechanism having a venting position in which the cartridge compartments are cut off from the static mixer and are in communication independently with respective venting outlets, and a dispensing position in which the cartridge compartments are in communication with the static mixer and are cut off from the venting outlets.

The provision of independent venting outlets in accordance with this aspect of the invention enables the unintended mixing of materials from the cartridge compartments, especially when the compartments are being filled, to be avoided.

Advantageously, the flow-directing mechanism also has a storage position in which the cartridge compartments are disconnected from the static mixer and from the venting outlets, enabling a syringe that has been filled to be stored temporarily if not required for immediate use.

The present invention further provides a syringe for dispensing a multi-component material, the syringe comprising:
a syringe cartridge having a first end and a second end, and respective compartments for components of the multi-component material; and
a plunger assembly that is movable into the syringe cartridge at the second end for dispensing material from the first end. The syringe cartridge is formed, at one end, with entry ports through which components of the multi-component material can be loaded into the compartments from a supply cartridge, the entry ports having upstanding collars for sealing to respective outlets of the supply cartridge, at least a portion of each upstanding collar being formed to be located inside the respective outlet of the supply cartridge, whereby material is removed from within the outlets when the syringe is removed from the supply cartridge.

The provision, in accordance with this aspect of the invention, of the upstanding collars on the syringe cartridge facilitates the positioning of the syringe cartridge on a supply cartridge from which material is to be loaded into the syringe. The subsequent automatic removal of material from within the outlets of the supply cartridge enables those outlets to be re-closed using conventional closure caps without displacing material for within the outlets, thereby avoiding the risk that the outlet area of the supply cartridge will be contaminated by the displaced materials mixing together and hardening.

A syringe in accordance with the invention may be a dental syringe, and may be of a size suitable for the intra-oral application of dental materials.

A syringe in accordance with the invention may be provided in the form of a unit-dose syringe.

A syringe in accordance with the invention may be formed from moulded components, preferably injection-moulded components.

In an embodiment of the invention in which the syringe comprises an inclined dispensing nozzle at the dispensing outlet of the static mixer, the dispensing nozzle may be integrally-formed with the static mixer.

In an embodiment of the invention in which the syringe cartridge comprises, at its outer surface, extensions and/or protrusions that are shaped to provide the cartridge, at least in places, with a substantially circular outer cross-section, those extensions and/or protrusions may be integrally-formed with the cartridge.

In an embodiment of the invention in which the syringe cartridge comprises a finger support, preferably two finger supports, for use in moving the plunger assembly into the cartridge, the finger support(s) may be integrally-formed with the cartridge.

By way of example, syringes constructed in accordance with the invention will now be described with reference to the accompanying drawings, in which.

Figure 1:
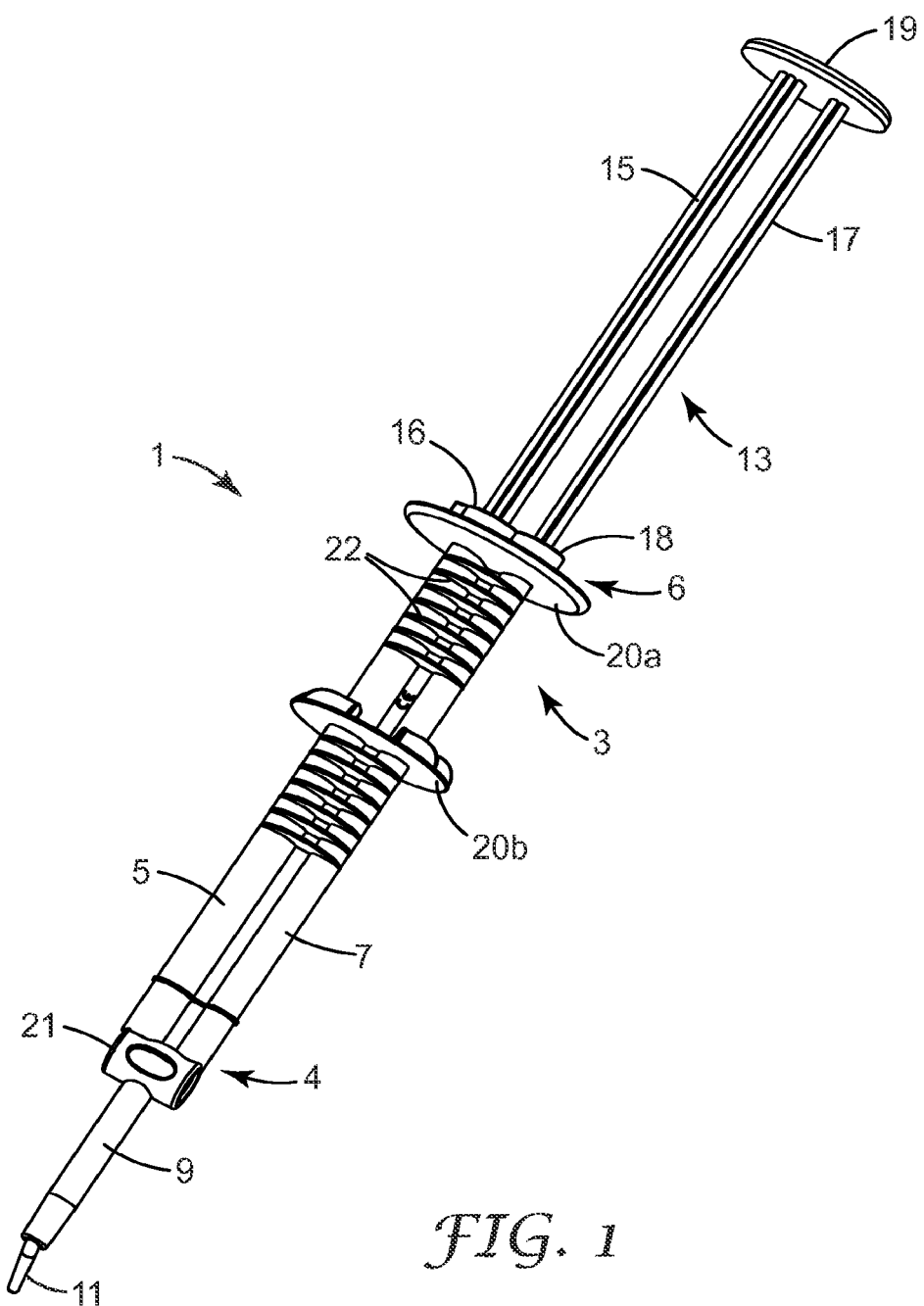
FIG. 1 is a perspective view of a unit-dose dental syringe in accordance with the invention, ready for use.

FIG. 1 shows a unit-dose syringe 1 ready for use in dispensing a multi-component dental material which, for the purposes of this description, is assumed to be a dental impression material comprising a mixture of a base paste and a catalyst. The syringe 1 comprises a cartridge 3 having two side-by-side compartments 5, 7. The compartment 5 is of larger volume than the compartment 7 and is filled with the base paste while the compartment 7 is filled with the catalyst. Within the cartridge 3, the compartments 5, 7 are separated from one another so that the base paste and catalyst contained within them do not mix prior to use of the syringe 1.

A static mixer 9 is connected at the front end (or first end) 4 of the cartridge 3 and has a dispensing nozzle (or mixer tip) 11 at its outlet end. As described in greater detail below, the static mixer 9 is pivotally-movable relative to the syringe cartridge but, when the syringe 1 is ready for use as shown in FIG. 1, is aligned with the longitudinal axis of the cartridge 3. The mixer tip 11 is an integral part of the static mixer 9 and, as shown, is directed at an angle relative to the longitudinal axis of the mixer.

A plunger assembly 13 extends into the cartridge 3 at the rear end (or second end) 6 of the latter. The plunger assembly comprises two pistons 15, 17 that extend into the cartridge compartments 5, 7 respectively through respective entry ports 16, 18. The pistons 15, 17 are connected together at the rear end of the plunger assembly 13 by a plunger plate 19, and have chamfered front tips 15a, 17a to assist in centring the pistons in the cartridge compartments 5, 7.

When the syringe is ready for use as shown in FIG. 1, the plunger plate 19 is used to move the plunger assembly 13 into the cartridge 3 to dispense material from within the compartments 5, 7 into the static mixer 9. Static mixers of various types suitable for use in dental syringes are known, some examples being described in the above-mentioned WO 2005/016170. As the pistons 15, 17 of the plunger assembly 13 move into the compartments 5, 7, the base paste and catalyst from the compartments pass along the bore of the static mixer 9 and are mixed together to form the impression material which is then dispensed from the mixer tip 11. The small size of the syringe 1 and the angle of the mixer tip 11 both facilitate the handling and the accurate positioning of the syringe so that the impression material can be dispensed directly into the mouth of a patient where it is required. After use, the syringe 1 can be discarded.

To assist in moving the plunger assembly 13 into the syringe cartridge 3, a conventional finger plate 20a is provided at the rear end of the cartridge to be gripped between the user's fingers while the thumb presses on the plunger plate 19. By way of further assistance in moving the plunger assembly 13, a second finger plate 20b is provided at a suitable point (for example, half-way) along the length of the syringe cartridge 3 and can be used instead of the first finger plate 20a if the user finds it more convenient. The second finger plate 20b may, for example, be used when the distance between the plunger plate 19 and the first finger plate 20a decreases to the point at which the angle between the user's thumb and fingers no longer enables good control to be maintained over the movement of the plunger assembly 13.

The handling of the syringe 1 is further assisted by a plurality of parallel plates 22 that are formed around the syringe cartridge 3, the plates being spaced apart from each other along the length of the cartridge and being shaped to provide the cartridge, in places, with a substantially circular outer cross-section and, more generally, with the feel of having a rounded outer surface. The plates 22 assist the user in rotating the syringe to achieve the optimum position of the mixer tip 11. As an alternative to the plates 22, any appropriately-shaped extensions or protrusions could be provided on the syringe cartridge 3, including flanges or ribs as described in the above-mentioned WO 2005/016170.

Figure 2:
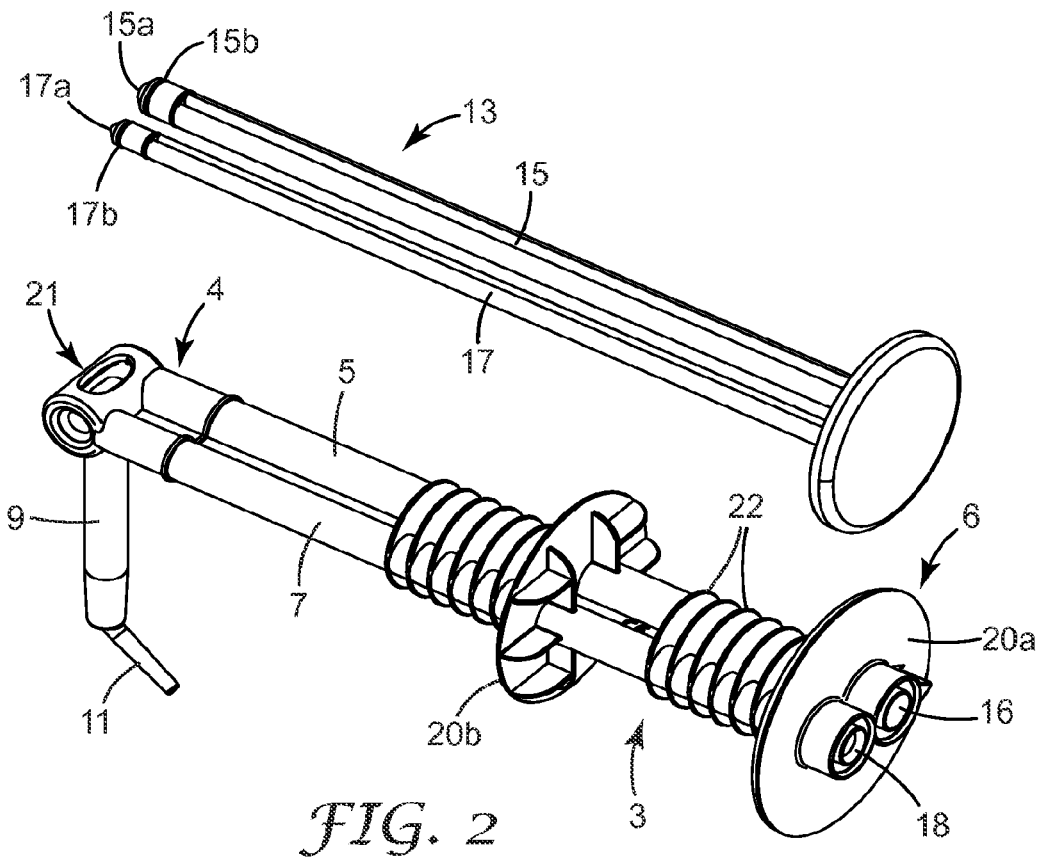
FIG. 2 shows the syringe in a disassembled condition, in preparation for filling the syringe cartridge.

Although unit-dose dental syringes can be provided already filled with the material to be dispensed, it is often desirable and more efficient if they can be filled as required by the end-user (i.e., in this example, within the dental surgery when a dental impression is about to be taken). With such a procedure in mind, the syringe 1 can be provided in a dismantled condition ready for filling. In this dismantled condition, shown in FIG. 2, the plunger assembly 13 is removed from the syringe cartridge 3, and the static mixer 9 is in a downwardly-directed position in which the bore of the mixer is cut off from the syringe compartments 5, 7. The form of the pivotal connection 21 between the static mixer 9 and the syringe cartridge 3 that enables this to be achieved will now be described with reference to FIG. 3.

Figure 3:
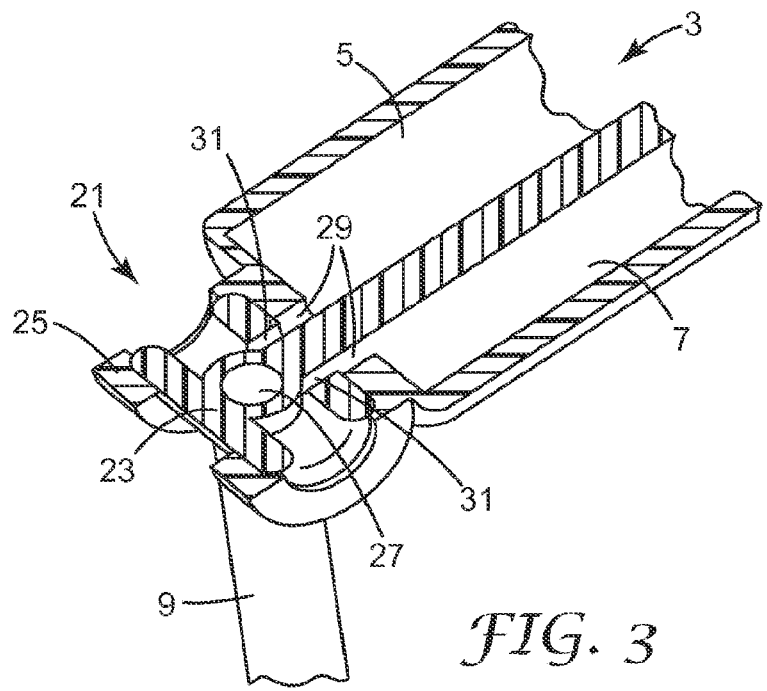
FIG. 3 shows a longitudinal cross-section through the flow-directing mechanism at the front end of the syringe cartridge, in the position shown in FIG. 2.

As shown in FIG. 3, the pivotal connection 21 comprises a cylindrical inner part 23 rotatable within an outer sleeve 25. The housing of the static mixer 9 extends radially from, and is formed integrally with, the inner part 23 of the pivotal connection 21, with the bore of the static mixer being extended, by a passageway 27, diametrically-across the inner part 23. The outer sleeve 25 of the pivotal connection, on the other hand, is an integral part of the syringe cartridge 3. The dispensing outlets 29 of the cartridge compartments 5, 7 extend through the sleeve 25 and, when the syringe 1 is ready for use (FIG. 1), they are aligned with the passageway 27 and, hence, connected to the bore of the static mixer 9. When, however, the static mixer 9 is in the downwardly-directed position shown in FIG. 2, the passageway 27 is moved out of alignment with the dispensing outlets 29 which are thereby cut off from the static mixer. Instead, the dispensing outlets 29 become aligned with respective vent holes (or venting outlets) 31 in the inner part 23 of the pivotal connection 21 and thereby connected to atmosphere via the open-ended interior of the inner part 23. This is the condition in which the syringe cartridge 3 is supplied to the end user. When the syringe is required for use, materials are loaded into the syringe compartments 5, 7 through the entry ports 16, 18 at the rear end of the compartments, followed by the insertion of the plunger assembly 13. Air that is displaced from within the compartments 5, 7 during this process can escape to atmosphere through the vent path provided by the dispensing outlets 29, the vent holes 31 in the inner part 23 of the pivotal connection 21, and the open-ended interior of the latter. In the event, however, of any material being discharged through the dispensing outlets 29 during the filling procedure, the risk of the materials from the two compartments 5, 7 coming into contact with one another is reduced because the presence of the passageway 27 ensures that the vent paths from the compartments are physically separated, with material from the compartments flowing out of respective ends of the inner part 23 of the pivotal connection 21. It will be appreciated that it is important to keep the materials from the compartments 5, 7 separate when the syringe is being filled because, if they do come into contact, they may start to harden and impair the operation of the syringe 1.

Figure 10:
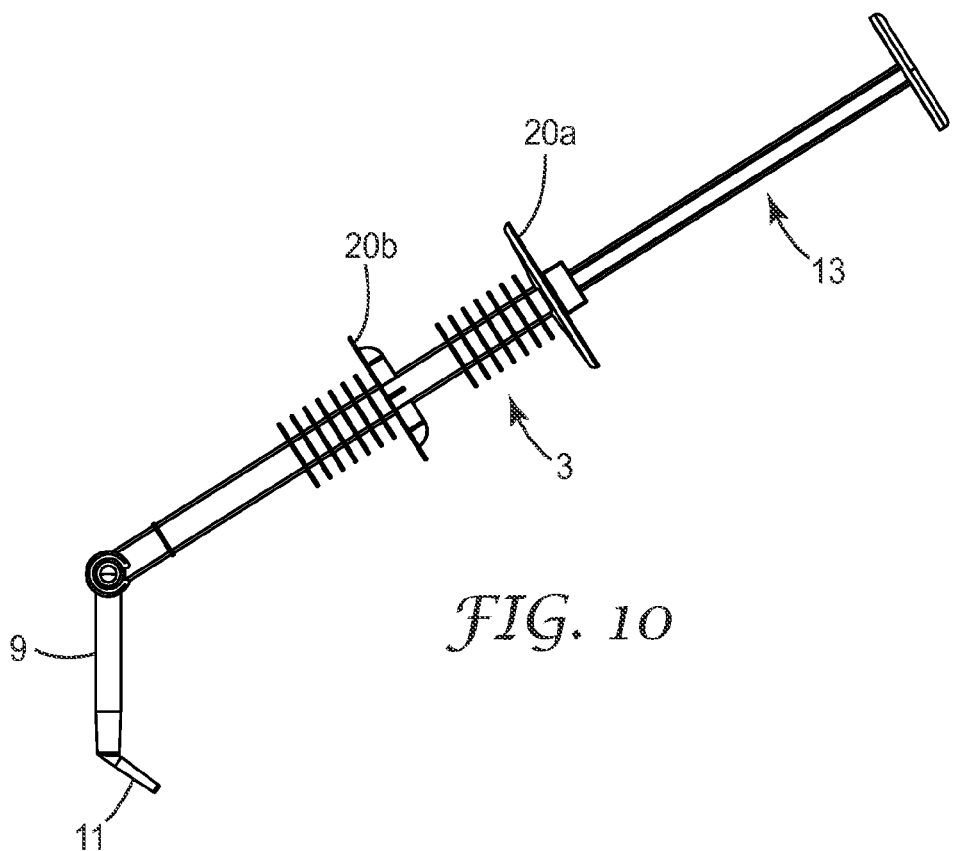
FIG. 10 is similar to FIG. 1 but shows the syringe in a storage condition.
Figure 11:
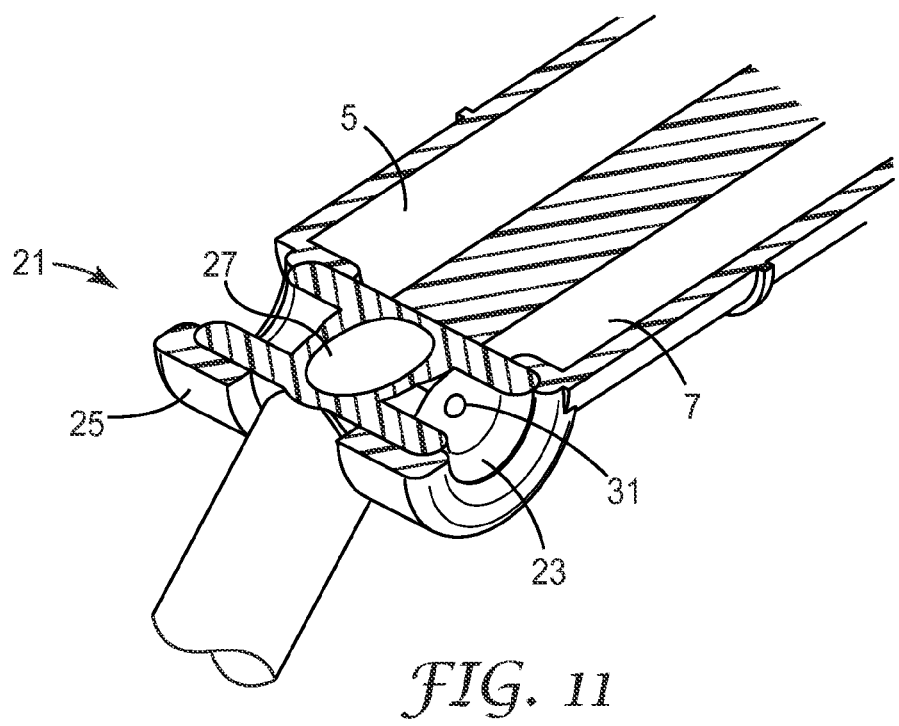
FIG. 11 is similar to FIG. 3 but shows the flow-directing mechanism in the position shown in FIG. 10.

When the syringe 1 has been filled, the static mixer 9 is pivoted into the position shown in FIG. 1 to bring the syringe into a ready-to-use condition. In some cases, however, it may be desirable to fill the syringe before it is actually required and, to permit the short-term storage of materials within the syringe, the pivotal connection 21 between the static mixer 9 and the syringe cartridge 3 can be provided with a third position intermediate the positions of FIGS. 1 and 2, in which the dispensing outlets 29 are blocked by the inner part 23 of the connection and thereby cut off from both the passageway 27 and the vent holes 31. This short-term storage position of the static mixer is illustrated in FIGS. 10 and 11.

The pivotal connection 21 between the static mixer 9 and the syringe cartridge 3 preferably ensures that the static mixer is held by friction in any of the selected positions described above and shown in FIGS. 1, 2 and 3, or 10 and 11.

Figure 4:
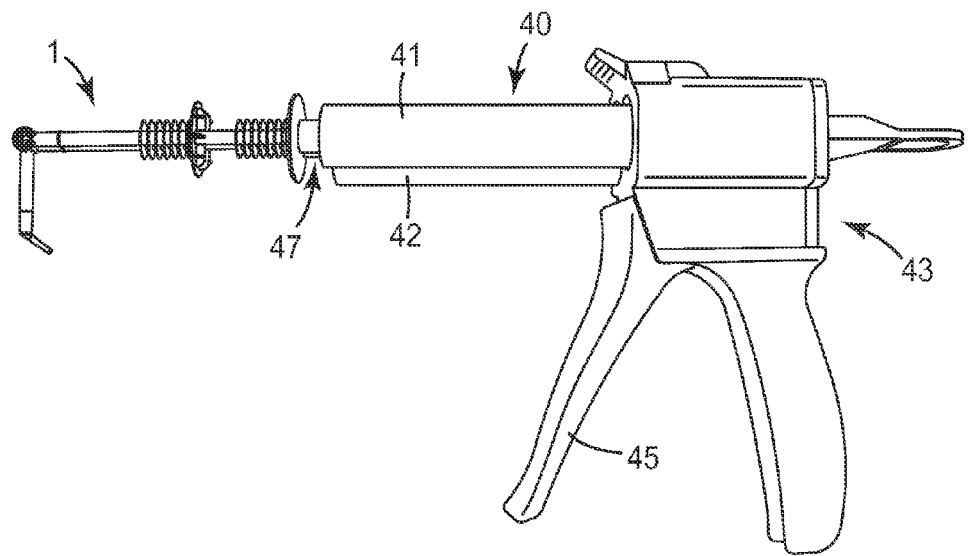
FIG. 4 is a general view showing the syringe cartridge being filled from a supply cartridge in an applicator.

FIG. 4 illustrates one method of loading material into the compartments 5, 7 of the syringe 1. In this case, both compartments are filled at the same time from a supply cartridge 40 comprising two cylinders 41, 42 containing, respectively, the catalyst and the base paste to be loaded into the syringe compartments 5, 7. The supply cartridge 40 may, for example, be a "Garant™" cartridge available from 3M ESPE AG of Seefeld, Germany. The supply cartridge 40 is located in a trigger-operated applicator 43 which may, for example, be a "Garant™" dispenser also available from 3M ESPE AG of Seefeld, Germany. Operation of the applicator trigger 45 causes a plunger (not visible) within the applicator 43 to expel material from the cylinders 41, 42 of the supply cartridge 40 through respective outlets 47.

The syringe cartridge 3, with the static mixer 9 in the filling position, is located on the end of the supply cartridge 40 with the entry ports 16, 18 of the cartridge positioned to receive material expelled through the outlets 47. This can be facilitated by the provision of upstanding collars 49, 51 which surround the entry ports 16, 18 and are advantageously configured, as described below, to enable the supply cartridge 40 to be closed cleanly after the syringe 1 has been filled. Preferably, as described below, the collars 49, 51 are also configured to accommodate supply cartridges 40 in which the outlets 47 are not both of the same size.

Figure 5:
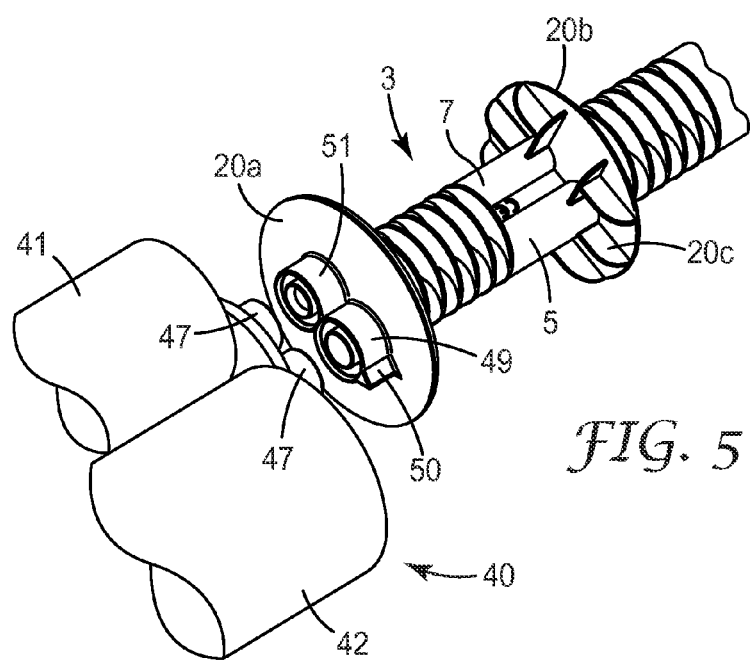
FIG. 5 is a perspective view showing the rear end of the syringe cartridge about to be connected to the outlet end of the supply cartridge.
Figure 6:
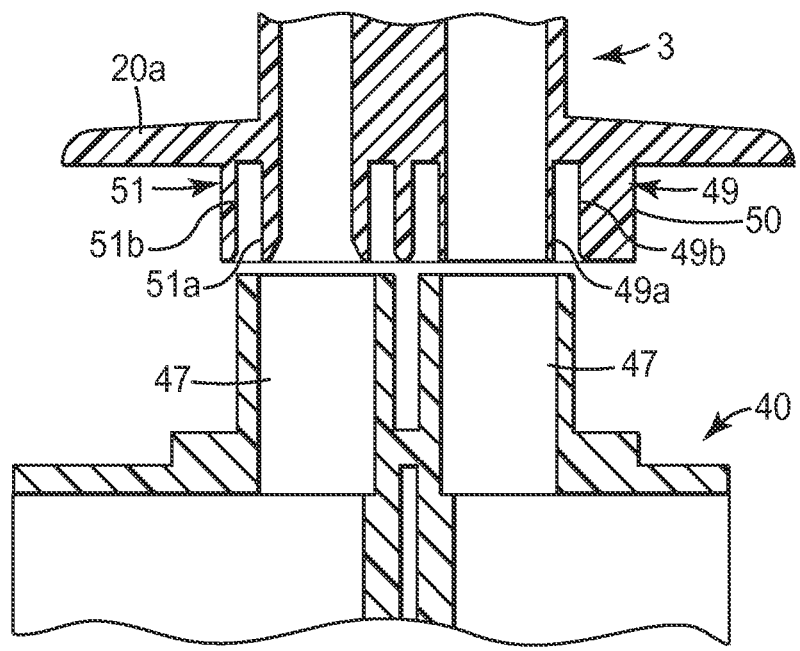
FIG. 6 shows a longitudinal cross-section through the rear end of the syringe cartridge and the outlet end of the supply cartridge in the situation of FIG. 5.

The upstanding collars 49, 51 of the entry ports 16, 18 can be seen in FIGS. 5 and 6, which show the rear end of the syringe cartridge 3 as it is about to be connected to the supply cartridge 40. Each collar comprises an inner part 49a, 51a and a concentric outer part 49b, 51b, intended to be located respectively within and around the corresponding outlet 47 of the supply cartridge 40 when the syringe is being filled. The outer parts 49b, 51b of the collars merge in the region between the entry ports 16, 18 although that is not essential. In addition, each collar 49, 51 is adapted, through the sizes of the inner and outer parts, to fit supply cartridge outlets of two different sizes as will be explained in greater detail below.

Figure 7:
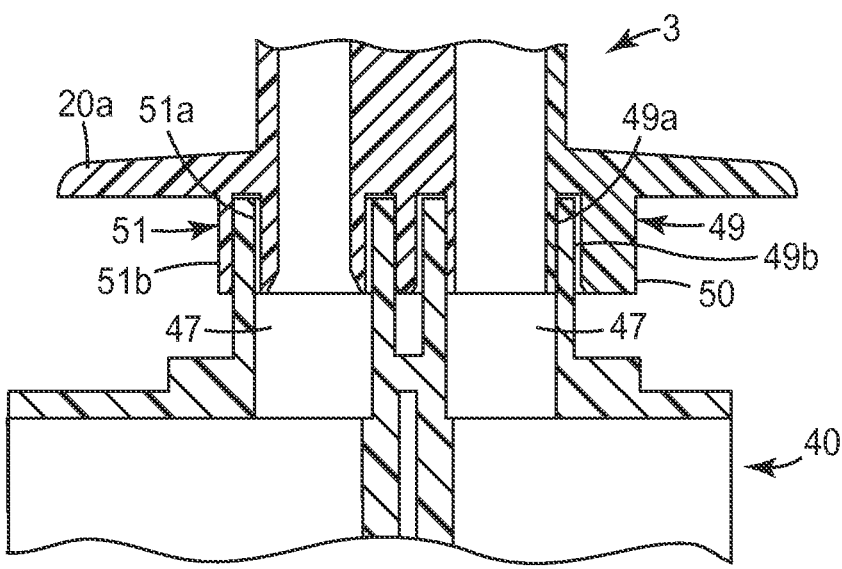
FIG. 7 is a longitudinal cross-section similar to FIG. 6 but showing the syringe cartridge connected to the supply cartridge.
Figure 8:
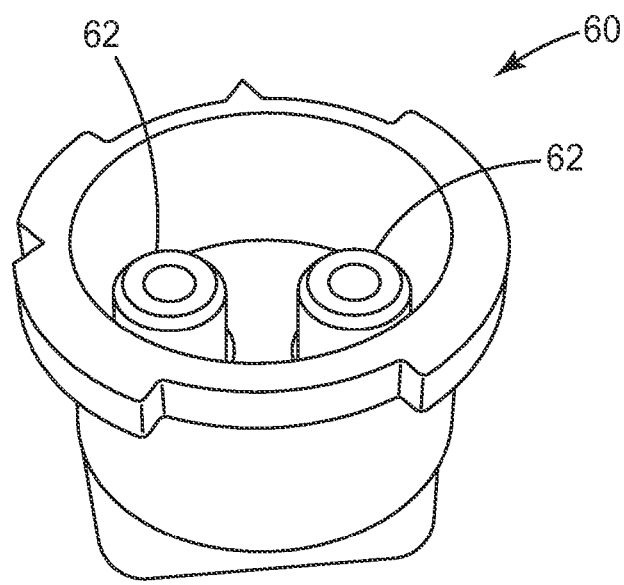
FIG. 8 is a perspective view of the closure cap of the supply cartridge of FIG. 7, showing the inside of the cap.

FIG. 7 shows, in cross-section, the syringe cartridge 3 located on a supply cartridge 40 having outlets 47 that are the same size as each other. The inner part 49a, 51a of each collar 49, 51 is located within the corresponding outlet 47 and, in this case, the outer diameter of the inner part 49a of collar 49 is such that it will seal against the inner surface of the corresponding outlet 47. For the collar 51, however, it is the inner surface of the outer part 51b that provides the seal to the corresponding outlet 47, in this case to its outer surface. The seals between the collars 49, 51 and the outlets 47 of the supply cartridge reduce the risk of material escaping around the outlets when the syringe is being filled. In addition, when the syringe cartridge 3 is removed from the supply cartridge 40, the material contained within the inner parts 49a, 51a of the collars will also be removed leaving a space within the outlets 47 of the supply cartridge so that the conventional closure cap of the supply cartridge can be replaced without causing material to spill out from the outlets. FIG. 8 shows such a conventional closure cap 60, and the two upstanding pins 62 inside the cap that are intended to fit inside the outlets 47 of the supply cartridge 40 when the closure cap 60 is replaced. It will be understood that, if the outlets 47 are full of material when the closure cap 60 is replaced, some of that material will be displaced by the pins 62 and could cause problems if material from the two outlets 47 were to mix and harden. A similar risk due to spillage of material from the collars 49, 51 of the syringe cartridge 3 when the plunger assembly 13 is inserted does not arise because only the chamfered tips 15a, 17a of the pistons 15, 17 could cause material to be displaced from the collars before the material becomes sealed within the compartments 5, 7 by the piston sealing rings 15b, 17b (see FIG. 2).

Figure 9:
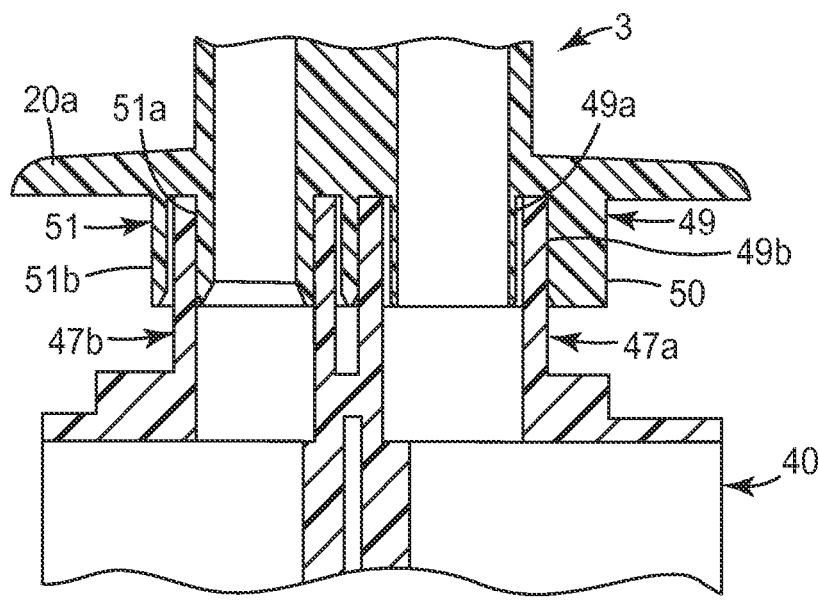
FIG. 9 is similar to FIG. 7 except that one of the outlet nozzles of the supply cartridge has a larger diameter than in FIG. 7.

FIG. 9 shows, in cross-section, an alternative situation in which the syringe cartridge 3 is located on a supply cartridge 40 having outlets that are a different size from each other and from the outlets of the supply cartridge shown in FIG. 7. More particularly, one of the outlets 47a of the supply cartridge of FIG. 8 has a greater diameter than the outlets 47 of FIG. 7 and the other outlet 47b has a smaller diameter than the outlets 47 of FIG. 7. Typically, the larger-diameter outlet 47a will be provided on a larger-volume cylinder of the supply cartridge 40 (containing, for example, the base paste component of an impression material) and the smaller-diameter outlet 47b will be provided on a smaller-volume cylinder of the supply cartridge (containing, for example, the catalyst component of an impression material).

In the situation illustrated in FIG. 9, the inner part 49a, 51a of each collar 49, 51 on the syringe cartridge 3 is again located within the corresponding outlet 47a, 47b of the supply cartridge 40. In this case, the inner surface of the outer part 49b of collar 49 will seal against the outer surface of the larger-diameter outlet 47a and the outer surface of the inner part 51a of collar 51 will seal against the inner surface of the smaller-diameter outlet 47b. The collars will, nevertheless, function as described above with reference to FIG. 7 to reduce the risk of material escaping around the outlets 47 when the syringe is being filled and, when the syringe cartridge 3 has been removed from the supply cartridge 40, to enable the closure cap of the supply cartridge to be replaced without causing material to spill out from the outlets 47a, 47b.

When the syringe cartridge 3 is filled from a supply cartridge 40 having outlets of a different size as shown in FIG. 9, an extension 50 on the collar 49 of the syringe cartridge mates with a corresponding cut-out (not visible) on the supply cartridge to ensure that the syringe cartridge is correctly oriented.

Figure 12:
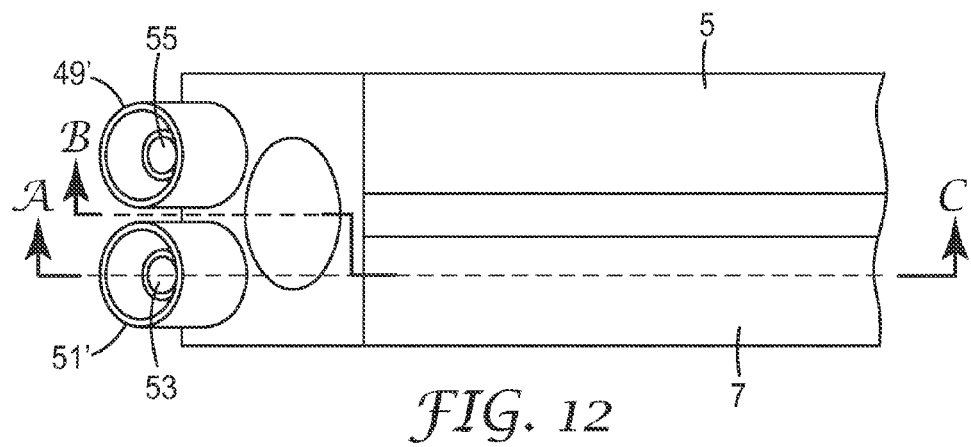
FIG. 12 is a plan view of the flow-directing mechanism at the front end of a modified syringe cartridge, in the filling position.
Figure 13:
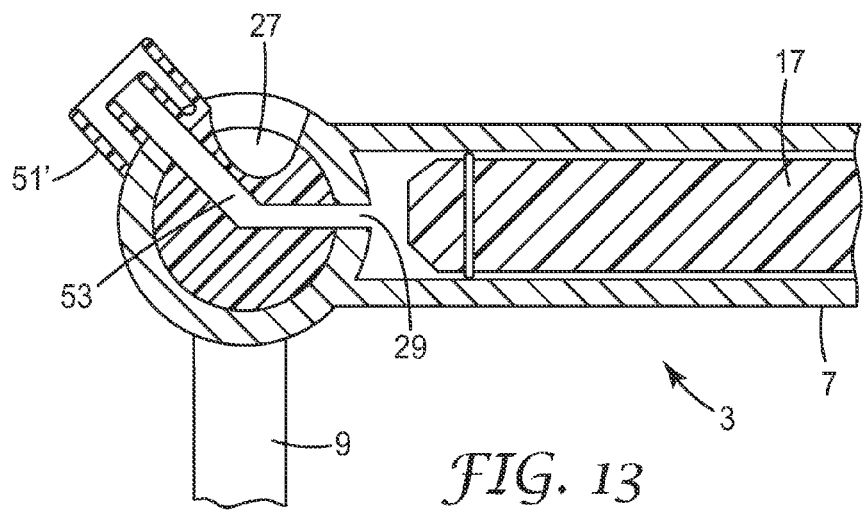
FIG. 13 shows a longitudinal cross-section on the line A-C in FIG. 11.
Figure 14:
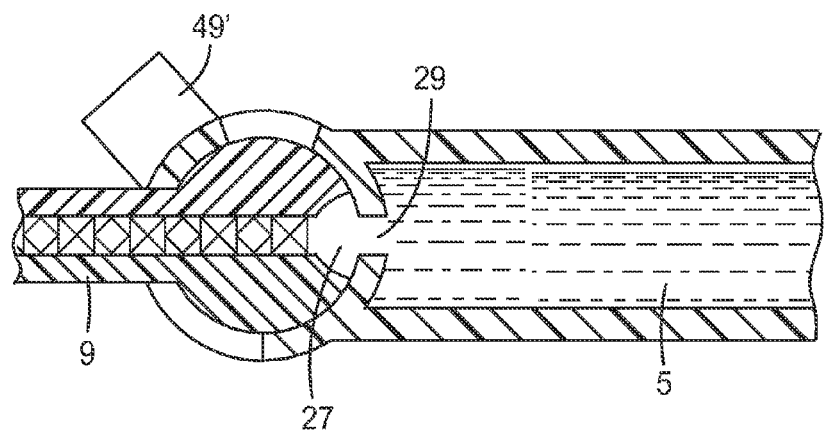
FIG. 14 shows a longitudinal cross-section on the line B-C in FIG. 11 when the syringe is in the ready-for-use condition.

FIGS. 12 to 14 illustrate a modification of the syringe 1 in which the cartridge compartments 5, 7 are filled from the front end of the syringe rather than the rear. In this case, the collars 49, 51 at the entry ports 16, 18 for the plunger assembly 13 are not required. Instead, similar collars 49', 51' are provided on the sleeve 25 of the pivotal connection 21 between the static mixer 9 and the syringe cartridge, where they surround the entrances to respective fill canals 53, 55 that extend through the inner part 23 of the pivotal connection as shown in FIG. 12. As will be apparent below, the vent holes 31 of FIG. 3 are not required in this modified version of the syringe and are omitted.

When it is required to load material into the compartments 5, 7 of the syringe cartridge of FIGS. 12 to 14, the static mixer 9 is in the position shown in FIGS. 12 and 13 (corresponding to the position shown in FIG. 2) to cut off the dispensing outlets 29 of the syringe compartments 5, 7 from the static mixer and align them instead with the fill canals 53, 55 respectively in the inner part 23 of the pivotal connection 21. The plunger assembly 13 (of which only the piston 17 is visible in FIG. 13) is also pushed completely into the syringe cartridge 3 at this stage. The collars 49', 51' are now located within and around the outlets 47 of the supply cartridge 40 as described above with reference to FIG. 7 or FIG. 9 as appropriate, and materials are loaded into the syringe compartments 5, 7 through the fill canals 53, 55 and the dispensing outlets 29 at the front end of the compartments, accompanied by movement of the plunger assembly 13 out of the syringe cartridge 3 at the rear end of the latter. When the syringe has been filled, the static mixer 9 is pivoted into the position shown in FIG. 14 to bring the syringe into the ready-to-use condition.

Figure 15:
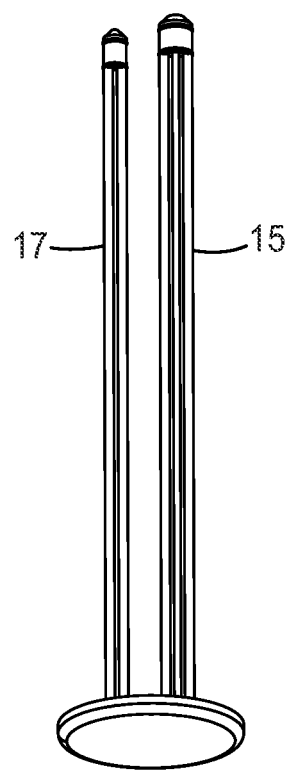
FIG. 15 shows a modified plunger assembly for the syringe of FIG. 1.

In some cases, when the syringe compartments 5, 7 have different internal volumes, it may be found that one compartment fills more quickly that the other despite the fact that the sizes of the compartments of the supply cartridge are adapted accordingly. This effect, which may for example be a result of the geometry of the collars 49, 51 on the syringe cartridge 3, can be compensated for by shortening the length of whichever piston of the plunger assembly 13 is intended to be inserted into the quick-filling compartment. FIG. 15, for example, shows a piston assembly 13 in which the piston 17 is shorter than the piston 15 to adapt the piston assembly to the situation in which the smaller-volume compartment 7 of the syringe fills more quickly from the smaller-volume cylinder 41 of the supply cartridge than the larger-volume compartment 5 fills from the larger-volume cylinder 42.

Although the syringe 1 has been described above with reference to multi-component dental impression materials, it will be understood that it could be used to dispense other materials and is not restricted either to use as a unit-dose syringe or to use in the dental field.

If, as preferred, the syringe cartridge 3 is an injection-moulded component, the thicknesses of the second finger plate 20b and the parallel plates 22 should be substantially less (e.g. less than half) the thickness of the walls of the syringe compartments 5, 7 to prevent the formation of sink marks on the inside of the compartments during the moulding process. If necessary, the second finger plate 20b can be reinforced by flanges 20c on its rear side as shown in FIG. 5.

It will be understood that certain features of the syringe 1 described above can, if required, be implemented in a syringe independently of the other features. Those features include, for example:

(i) the vent holes 31 that are used when the syringe cartridge 3 is filled from the rear end;
(ii) the upstanding collars 49, 51 (or 49', 51') that are used to connect the syringe cartridge to a supply cartridge;
(iii) the second finger plate 20b that assists in handling the syringe; and
(iv) the plates 22 that also assist in handling the syringe.

When provided in combination as described above, however, the resulting syringe is easy to fill when required for use, without risk of the component materials in the syringe compartments coming into contact with each other prematurely; and easy to handle so that material can be dispensed in a controlled manner and accurately to the required location.

The invention claimed is:

1. A syringe for dispensing a multi-component material, the syringe comprising:
   a syringe cartridge having a first end and a second end, and respective compartments for components of the multi-component material;
   a static mixer connected to the first end of the cartridge, the mixer having a dispensing outlet; and
   a plunger assembly that is movable into the syringe cartridge at the second end to dispense material from the first end;
   wherein the connection between the static mixer and the first end of the syringe cartridge comprises a flow-directing mechanism configured to be selectively positioned between a venting position in which each of the cartridge compartments is cut off from the static mixer and at the same time is in communication independently with a respective venting outlet, and a dispensing position in which each of the cartridge compartments is in communication with the static mixer and at the same time is cut off from the respective venting outlet.

2. A syringe as claimed in claim 1, in which the flow-directing mechanism also has a storage position in which the cartridge compartments are cut off from the static mixer and from the venting outlets.

3. A syringe as claimed in claim 1, in which the static mixer is pivotally-movable relative to the cartridge to change the position of the flow-directing mechanism.

4. A syringe as claimed in claim 1, the syringe cartridge being formed, at the second end, with entry ports through which components of the multi-component material can be loaded into the compartments from a supply cartridge, wherein each entry port has an upstanding collar for sealing to a respective outlet of the supply cartridge, at least a portion of each upstanding collar being formed to be located inside the respective outlet of the supply cartridge, whereby material is removed from within the outlets of the supply cartridge when the syringe is removed from the supply cartridge.

5. A syringe as claimed in claim 4, in which the entry ports also provide access for the plunger assembly into the syringe cartridge.

6. A syringe for dispensing a multi-component material, the syringe comprising:
   a syringe cartridge having a first end and a second end, and respective compartments for components of the multi-component material;
   a static mixer connected to the first end of the cartridge, the mixer having a dispensing outlet; and
   a plunger assembly that is movable into the syringe cartridge at the second end for dispensing material from the first end;
   wherein the connection between the static mixer and the first end of the syringe cartridge comprises a flow-directing mechanism configured to be selectively positioned between a venting position in which each of the cartridge compartments is cut off from the static mixer and at the same time is in communication independently with a respective venting outlet, and a dispensing position in which each of the cartridge compartments is in communication with the static mixer and at the same time is cut off from the respective venting outlet; and
   wherein the syringe cartridge is formed, at one end, with entry ports through which components of the multi-component material can be loaded into the compartments from a supply cartridge, the entry ports having upstanding collars for sealing to respective outlets of the supply cartridge, at least a portion of each upstanding collar being formed to be located inside the respective outlet of the supply cartridge, whereby material is removed from within the outlets when the syringe is removed from the supply cartridge,
   wherein each collar comprises two cylinders, one cylinder being disposed around the other whereby it will be located around an outlet of the supply cartridge when the inner cylinder is located within the outlet.

7. A syringe as claimed in claim 6, further comprising a static mixer connected to the first end of the cartridge, the mixer having a dispensing outlet; wherein the connection between the static mixer and the first end of the syringe cartridge comprises a flow-directing mechanism having a filling position in which the cartridge compartments are cut off from the static mixer, and a dispensing position in which the cartridge compartments are in communication with the static mixer.

8. A syringe as claimed in claim 7, in which the entry ports are located at the first end of the syringe cartridge, the cartridge compartments being in communication independently with respective ones of the entry ports when the flow-directing mechanism is in the filling position, and cut off from the entry ports when the flow-directing mechanism is in the dispensing position.

9. A syringe as claimed in claim 8, in which the flow-directing mechanism also has a storage position in which the cartridge compartments are cut off from the static mixer and from the entry ports.

10. A syringe as claimed in claim 8, in which the static mixer is pivotally-movable relative to the cartridge to change the position of the flow-directing mechanism.

11. A syringe as claimed in claim 4, wherein each upstanding collar provides surfaces capable of sealing to differently-sized outlets of supply cartridges.

12. A syringe as claimed in claim 11, in which each collar comprises two cylinders, one cylinder being disposed around the other whereby it will be located around an outlet of the supply cartridge when the inner cylinder is located within the outlet, the inner surface of the outer cylinder and the outer surface of the inner cylinder being capable of sealing to differently-sized outlets of supply cartridges.

13. A syringe as claimed in claim 6, in combination with a supply cartridge having outlets engageable with the entry ports of the syringe cartridge.

14. A syringe as claimed in claim 1, further comprising a dispensing nozzle at the dispensing outlet of the static mixer, the nozzle being inclined relative to the longitudinal axis of the static mixer.

15. A syringe as claimed in claim 14, in which the cartridge comprises, at its outer surface, extensions and/or protrusions that are shaped to provide the cartridge, at least in places, with a substantially circular outer cross-section.

16. A syringe as claimed in claim 15, in which the extensions and/or protrusions comprise a plurality of parallel plates that encircle the cartridge, the plates being located at intervals along the cartridge between the first and second ends.

17. A syringe as claimed in claim 16, in which the cartridge and the plates are an integrally-moulded component.

18. A syringe as claimed in claim 1, comprising two finger supports for use in moving the plunger assembly into the cartridge, the finger supports being spaced apart from each other in the direction of travel of the plunger assembly.

19. A syringe as claimed in claim 18, in which the finger supports are located on the cartridge.

20. A syringe as claimed in claim 19, in which the finger supports and the cartridge are an integrally-moulded component.

21. A syringe as claimed in claim 1, in which the cartridge comprises two compartments having different internal volumes, and the plunger assembly extends into the smaller-volume compartment for a smaller distance.

* * * * *